United States Patent [19]
Bahl et al.

[11] Patent Number: 5,215,882
[45] Date of Patent: Jun. 1, 1993

[54] METHOD OF IMMOBILIZING NUCLEIC ACID ON A SOLID SURFACE FOR USE IN NUCLEIC ACID HYBRIDIZATION ASSAYS

[75] Inventors: Chander Bahl, Flemington; Rhonda Lang, Lawrenceville, both of N.J.; Leopoldo G. Mendoza, Madison, Wis.

[73] Assignee: Ortho Diagnostic Systems, Inc., Raritan, N.J.

[21] Appl. No.: 444,031

[22] Filed: Nov. 30, 1989

[51] Int. Cl.$^5$ .............................................. C12Q 1/68
[52] U.S. Cl. ...................................... 435/6; 435/810; 436/518; 436/530; 436/808; 935/77; 935/78
[58] Field of Search ........................ 435/6, 174, 810; 935/77, 78, 108; 436/178, 518, 530, 808; 424/78, 82

[56] References Cited

U.S. PATENT DOCUMENTS

| | | | |
|---|---|---|---|
| 4,423,208 | 12/1983 | Grandics | 536/5 |
| 4,687,808 | 8/1987 | Jarrett et al. | 424/78 |

FOREIGN PATENT DOCUMENTS

| | | |
|---|---|---|
| 0131546 | 1/1985 | European Pat. Off. |
| 0136153 | 4/1985 | European Pat. Off. |
| 0174879 | 3/1986 | European Pat. Off. |
| 0209996 | 1/1987 | European Pat. Off. |
| 0308206 | 3/1989 | European Pat. Off. |
| 04674 | 10/1985 | PCT Int'l Appl. |
| 01302 | 2/1988 | PCT Int'l Appl. |
| 2197720 | 5/1988 | United Kingdom |

OTHER PUBLICATIONS

European Search Report, EP 90 31 3007, Mar. 28, 1991.
Wreschner, D. H. and Herzberg, M, Nucleic Acids Research 12: 1349–1359, (1984).
Gebeyechu et al., Nucleic Acids Research 15: 4513–4525, (1987).
Froehler, B. C., Tetrahedron Letters 27: 5575–5578 (1986).

*Primary Examiner*—Amelia Burgess Yarbrough

[57] ABSTRACT

Methods of immobilizing nucleic acid on a solid surface for us in nucleic acid hybridization assays is disclosed. The methods of the invention comprise reacting a modified nucleic acid strand comprising a variable portion and an anchor portion wherein the variable portion comprises a nucleotide sequence having a selected base sequence and the anchor portion comprises at least one nucleotide base modified with a primary amine function or nucleotide base equivalent having a primary amine function and reacting the modified nucleic acid strand with a free aldehyde group of the solid surface in the presence of a reducing agent to form complexes of the modified nucleic acid strand and at least a portion of the free aldehyde groups on the solid surface.

22 Claims, No Drawings

METHOD OF IMMOBILIZING NUCLEIC ACID ON A SOLID SURFACE FOR USE IN NUCLEIC ACID HYBRIDIZATION ASSAYS

FIELD OF THE INVENTION

The present invention relates to methods for immobilizing nucleic acids to solid surfaces for nucleic acid hybridization assays.

BACKGROUND OF THE INVENTION

Nucleic acid hybridization assays have proven useful in detecting the presence of microorganisms in biological samples (tissue, blood, urine, saliva, etc.) to diagnose infection and for detecting the presence in a mixture of a nucleic acid sequence of interest.

Nucleic acid hybridization assays are generally performed by immobilizing the test nucleic acid strand on a solid surface. A mixture containing the labeled complementary nucleic acid strand is contacted with the immobilized nucleic acid strand under conditions allowing hybridization of the two complementary strands. The hybridization of the two strands is then detected by chemical or other means by detecting the label on the probe strand. Alternatively, the nucleic acids are detected by sandwich hybridization techniques in which one set of sequences complementary to the target sequence is immobilized onto a solid surface. The surface is then contacted with the targer DNA and a labeled probe complementary to the target at a place different than the one attached to the solid surface. Under appropriate conditions the labeled probe is retained on the paper via the target DNA and detected by chemical or physical methods directly or indirectly.

Nucleic acids are typically immobilized on solid surfaces such as cellulose or nylon by physical contact with the surface, and the nucleic acids are bound to the surface through weak non-covalent bonds. Because of the nonspecific binding of nucleic acid to these surfaces, it is difficult to orient the nucleic acid so that it does not interact with the solid surface with the portions of the nucleic acid that are needed to hybridize with the test sequences. Thus greater amounts of the nucleic acid are needed to ensure a sufficient amount of free sequences to bind to the test nucleic acid. This inefficient use of nucleic acid can be expensive and can be limiting if only small quantities of the nucleic acid are available.

Additionally, the inability to accurately place the nucleic acid on the solid surface can hinder the effectiveness of the assay when small amounts of the nucleic acid sequence of interest are present, since it can be difficult to distinguish the nucleic acid present from background reactions.

Further, it would be desirable to be able to test for more than one pathogen in a single assay, or to test for more than one nucleic acid sequence in a single microorganism in the same assay. Uncertain placement of nucleic acids on the solid surface is a drawback to the development of assays of this kind.

SUMMARY OF THE INVENTION

The methods of the invention provide methods of immobilizing nucleic acid to a solid surface having a free aldehyde group for use in nucleic acid hybridization assays. In the methods of the invention a modified nucleic acid strand comprising a variable portion and an anchor portion wherein the variable portion comprises a nucleotide sequence having a selected base sequence and the anchor portion comprises at least one nucleotide base modified with a primary amine function or nucleotide base equivalent having a primary amine function is reacted with the free aldehyde group of the solid surface in the presence of a reducing agent to form complexes of the modified nucleic acid strand and at least a portion of the free aldehyde groups.

Accordingly, the invention also provides solid surfaces for performance of nucleic acid hybridization assays comprising a solid surface prepared in accordance with the methods of the invention. The invention further provides kits for performance of nucleic acid hybridization assays comprising a solid surface of the invention and at least one labeled nucleic acid probe, the solid surface and the probe selected to form a detection system for a target strand of nucleic acid.

The methods of the invention provide an efficient procedure for immobilizing nucleic acids, especially oligonucleotides, on to solid surface without affecting their ability to hybridize to complementary nucleic acid. The method is fast, economical and efficient. On flat surfaces such as paper or membranes, the oligonucleotides can be applied in zones alone, together with, or alongside other oligonucleotides or proteins such as enzymes or antibodies. The immobilization occurs via synthetic anchors provided at the termini of the oligonucleotide being immobilized.

The methods and solid surfaces of the invention provide specific orientation of the immobilized nucleic acid by the anchor portion so that the entire or substantially all of the variable portion is free to hybridize with test nucleic acid. This improvement over prior methods of immobilizing nucleic acids on solid surfaces for nucleic acid hybridization provided by the methods and solid surfaces of the invention allows more efficient use of the immobilized nucleic acid. Smaller quantities are needed as non-specific binding of the nucleic acid to the solid support is eliminated through the binding of the anchor portion with the solid support.

The methods of the invention make it possible to place the immobilized nucleic acid in pre-determined positions on the surface, facilitating detection of hybridized test nucleic acid by allowing it to be more easily distinguished from background reactions. Additionally, controlled placement of the immobilized nucleic acid allows the immobilization of more than one type of nucleic acid sequence in precise locations on the solid surface, so that more than one type of microorganism or nucleic acid sequence of interest can be detected in the same assay.

The solid surfaces of the invention have the advantage of providing a light, or paper colored, background which gives a good contrast for hybridization assays performed on the solid surface.

DETAILED DESCRIPTION OF THE INVENTION

In the methods of the invention nucleic acid is immobilized on a solid surface through covalent bonding. The methods of the invention produce a solid surface having nucleic acid, DNA or RNA, bound thereon in a predetermined pattern that is suitable for use in nucleic acid hybridization assays.

In preferred embodiments, DNA or RNA to be immobilized is adapted for immobilization by first attaching at least one nucleotide base modified with a primary amine function or nucleotide base equivalent having a primary amine function at either of the termini of the DNA or RNA to form modified nucleic acid strands. The modified nucleic acid strand thus formed comprises a variable portion and an anchor portion wherein the variable portion comprises a nucleotide sequence having a selected base sequence and the anchor portion comprises at least one nucleotide base modified with a primary amine function or nucleotide base equivalent having a primary amine function attached at either terminus of the variable portion.

The modified nucleic acid strands to be immobilized and used for capturing or hybridizing with complementary nucleic acids are preferably prepared by chemical synthesis using a DNA synthesizer and commercially available reagents. The base sequence of the variable portion of the modified nucleic acid strand is selected in accordance with the organism it is desired to detect, or other purpose for the hybridization assay. The variable portion is preferably prepared by chemical synthesis, however, it can also be prepared from natural cellular or recombinant sources using recombinant techniques. The variable portion may be derived from human, bacterial, viral, fungal or other sources. If the variable portion is prepared from cellular or recombinant sources, synthesis of the variable portion will not be necessary. The variable portion may also be a homopolymer, such as oligo thymidine (poly thymidine or poly T) or poly adenine (Poly A). The variable portion is preferably from about two to about 1,000 nucleotide bases in length, more preferably from about 15 to about 100 nucleotide bases in length.

The anchor portion is added to the variable portion. The anchor portion may be added to either the 3' or 5' terminus of the variable portion. The anchor portion is preferably comprised of at least one nucleotide base modified with a primary amine function or nucleotide base equivalent having a primary amine function more preferably of from two to about ten nucleotide bases or nucleotide base equivalents, and most preferably of from about five to about eight nucleotide bases or nucleotide base equivalents. Suitable nucleotide bases include cytosine modified at the 4 position of the pyrimidine ring, adenine modified at the 6 position of the purine ring, and uridine modified to contain a primary amino function. Examples of suitable modified nucleotide bases include 5-amino(12)-2'-deoxyuridine-5'-triphosphate (Behring Diagnostics, La Jolla, Calif.), 5-(3-aminoallyl)-2'-deoxyuridine 5'-triphosphate, 5-(3-aminoallyl)uridine 5'triphosphate, and N6-([6-aminohexyl]-carbamoylmethyl)-adenosine 5'triphosphate (Sigma Chemical, St. Louis, Mo.). Other nucleotide bases modifed to contain a primary amine function may also be suitable for use in the anchor portion. A preferred amino-modified nucleotide base is cytosine modified at the 4 position of the pyrimidine ring. Nucleotide base equivalents include phosphoramidites, phosphonates that can be modified with primary amines to give phosphoramidates, and other compounds having, or capable of being modified to contain, primary amine functions that can be substituted for nucleotide bases in a nucleic acid sequence or that can be added at the 3' or 5' ends of a nucleic acid sequence.

The anchor portion is attached to the variable portion by covalent bonding through the synthetic process using a DNA synthesizer or through any conventional means for ligation of nucleic acids; for example, ligase enzymes such as T$_4$ DNA ligase and *E. coli* ligase; chemical means (Z. A. Shabarova, M. S. Ivanovskaya and M. G. Isaguilantis, FEBS Letters, vol. 154, number 2, Apr. 1983); and photoligation means ("DNA Assay Using Template-Directed Photoligation'" San Diego Section of the American Association of Chemical Industry-AMOCO Technology Company, P.O. Box 400 Naperville, Ill. 60566). Phosphoramidites may be added to the variable portion using conventional phosphoramidite chemistry. Phosphonates that can be modified with primary amines to give phosphoramidates may be attached to the variable portion according to the method of Froehler, Tetrahedron Letters 27(46): 5575–5578 (1983).

In a preferred embodiment of the invention, the anchor portion of the modified nucleic acid strand comprises cytosine modified at the 4 position of the pyridine ring with a primary amine function. The preferred anchor portion is prepared by chemical synthesis in which cytosine is attached to the variable portion by covalent bonding. The cytosines of the anchor portion are then subjected to bisulfite catalyzed transamination reaction with a diamine. The transamination reaction results in modification of the primary amine group at the 4 position of the cytosine pyrimidine ring with the diamine which has a primary amine substituent. Diamines having from about two to about ten carbon atoms, preferably from about five to about seven carbon atoms, are suitable for use in the invention. In preferred embodiments hexanediamine is employed. Transamination of cytosine at the exocyclic animo group at the 4 position on the pyrimidine ring may be accomplished by conventional transamination methods, such as the method described herein.

If the variable portion of the modified nucleic acid strand contains cytosine, it will be necessary to protect the first variable portion during transamination, so that any cytosines present in this portion are not modified, thus interfering with later hybridization with the test nucleic acid sequence. Protection of cytosine in the variable portion can readily be provided by hybridizing a complementary sequence to this portion of the modified nucleic acid strand, taking care to exclude the anchor portion. The complementary protective strand may be prepared by chemical synthesis, or purified from natural or recombinant sources using any convenient means. It is important that only the anchor portion cytosine molecules are single stranded and that the other cytosines in the variable portion are protected from modification by transamination by hydrogen bonding with the complementary strand. The complementary strand is removed from the modified nucleic acid strand before a hybridization assay is performed. Denaturing of the protective strand may be accomplished by any conventional means such as alkaline conditions or elevated temperatures and removal may be accomplished by any suitable purification technique, such as chromatography methods and the like, or by rinsing the solid surface if removal of the complementary protective strand takes place after immobilization of the modified nucleic acid strand. The complementary protective strand may be removed after the modification step, or after any subsequent step of the methods of the invention.

The modified nucleic acid strand is applied to a solid surface containing aldehyde groups, in the presence of a reducing agent such as sodium cyanoborohydride. A mixture of the modified nucleic acid strand and reducing agent in a liquid such as water or phosphate buffer having a pH in the range of from about 6.0 to about 8.5, preferably about 7.6, is applied to the aldehyde surface by spraying, soaking or any convenient method. The concentration of modified nucleic acid strand in the mixture should be great enough to ensure detection in a nucleic acid hybridization assay. Generally, a concentration of modified nucleic acid strand in the range of 50 p moles to 150 p moles per square centimeter of solid surface, preferably a concentration of about 100 p moles per square centimeter will given an easily detectable result under assay conditions. The actual concentration used, however, will depend on the method of application and the surface to be coated, more concentrated solution is preferred so as to avoid the lateral movement of the solution on the surface.

Solid surfaces suitable for use in the methods of the invention are those containing a free aldehyde group, or which can be modified to contain a free aldehyde group. For example, cellulose paper can be modified by limited oxidation with periodate to contain free aldehyde groups. Cellulose paper having free aldehyde groups may also be purchased from commercial sources such as Sterogene Biochemicals, San Gabriel, Calif.

The modified nucleic acid strand may be positioned on the solid surface by any suitable method. For application to the solid surface, the modified nucleic acid strand will typically be in a liquid solution which may be applied to the solid surface by any convenient method including, manual application of the liquid solution, spraying, or by dipping the solid surface into the solution containing the modified nucleic acid strand. The modified nucleic acid strand may be applied to the solid surface in any desired pattern or combination of patterns. More than one type of DNA sequence can be positioned on the solid surface; for instance a nucleic acid sequence unique to microorganism A and a nucleic acid sequence unique to microorganism B can be immobilized in discrete stripes onto the solid surface to detect microorganisms A and B in the same hybridization assay by using appropriately labeled probes.

The modified nucleic acid strand and reducing agent is allowed to incubate with the solid surface for a length of time sufficient for the reaction between the nucleic acid and diamine to take place. Depending on the reducing agent and transamination method used this time will be approximately two hours. At the end of the incubation period, the solid surface is washed with water or a buffer such as phosphate buffered saline (PBS) to remove all excess reagents and finally washed with a buffer such as PBS. The solid surface is then dried by any convenient method, such as blotting between filter paper, or over a desiccant.

To reduce background interference in a hybridization assay, aldehyde groups on the solid surface that did not react with the modified nucleic acid strand may be optionally modified by reaction with an amino acid, such as $\alpha$-amino caproic acid in the presence of a reducing agent. This step will convert the remaining aldehyde groups to acidic functions by reaction with the acid, so that the aldehyde groups will not be available to bind with nucleic acid or other reagents in nucleic acid hybridization assays and also introduces a negative charge on the surface, which aids in keeping background interference low. Conversion of unreacted aldehyde groups may readily be accomplished after immobilization of the modified nucleic acid strand by applying a mixture of 0.1 M aminocaproic acid and 0.1 M sodium cyanoborohydride to the solid surface. The mixture may be applied to the solid surface by soaking the solid surface in a solution containing $\alpha$-amino caproic acid and sodium cyanoborohydride, spraying or any other suitable method. After approximately one-half to two hours the paper is washed with water few times to remove all reagents and finally with phosphate buffered saline (PBS) and dried and stored.

The kits of the invention comprise a solid surface of the invention and at least one labeled nucleic acid probe. The solid surface and the labeled nucleic acid probe are selected to form a detection system for target nucleic acid. For example, to detect nucleic acid sequence A from microorganism A, a solid surface of the invention having the variable portion of the modified nucleic acid strand complementary to at least a portion of nucleic acid sequence A would be provided in the kit. A labeled nucleic acid probe complmentary to a different portion of nucleic acid sequence A would then be provided for detection of nucleic acid sequence A hybridized to the solid surface.

Nucleic acid sequences useful in the labeled nucleic acid probes are readily prepared by any conventional method such as organic synthesis, recombinant DNA techniques or isolation from genomic DNA. However, these sequences are particularly amenable to organic synthesis using techniques known in the art such as techniques utilizing a nucleic acid synthesizer and commercially available reagents.

The labeled nucleic acid probes may be labeled by conventional radioisotopic labeling, chemical labeling, immunogenic labeling, or a label with light scattering effect, and the like. Suitable methods to detect such labels are scintillation counting, autoradiography, fluorescence measurement, calorimetric measurement, or light emission measurement.

Thus, the labeling may comprise a radiolabel (e.g. $^{14}C$, $^{32}P$, $^{3}H$, and the like), an enzyme (e.g., peroxidase, alkaline or acid phosphatase, and the like), a bacterial label, a fluorescent label, an antibody (which may be used in a double antibody system), an antigen (to be used with a labeled antibody), a small molecule such as biotin (to be used with an avidin, streptavidin, or antibiotin system), a latex particle (to be used in a buoyancy or latex agglutination system), an electron dense compound such as ferritin (to be used with electron microscopy), or a light scattering particle such as colloidal gold, or any combinations or permutations of the foregoing.

For example, if the labeling portion of the probe is an antigen, a signal can be generated by complexing said antigen with an antibody/enzyme conjugate, followed by addition of an enzyme substrate. If this portion were an antibody, signal can be generated by complexing anti-antibody or an $F_c$ binding protein such as Protein A therewith, when such second antibody or Protein A have been conjugated to an enzyme.

For reasons of ease and safety in the handling of the probe, it is preferred that it be chemically labeled, especially enzymatically or immunologically. In more preferred embodiments, the chemical label of choice is a hapten such as biotin, iminobiotin, fluorescein and the like.

Among the preferred labeling systems that may be mentioned are those based on the biotin/strepavidin system. This system can be incorporated into the probe by a variety of means. For example, the probe can be covalently attached to biotin via a cytochrome c bridge (Manning et al, Biochemistry, 16:1364-1370 (1977), Manning et al, Chromosoma, 53:107-117 (1975), Sodja.

A., Nucleic Acids Research, 5:385–401 (1978)), or the biotin can be covalently incorporated into specific nucleotide residues (Langer, P. R., Proceedings of one National Academy of Sciences, USA, 78:6633–6637 (1981), or the biotin can be attached to a polynucleotide by means of a diamine (e.g., pentane diamine) bridge (Broker, T. R., et al. Nucleic Acids Research 5:363–384 (1978)). Interaction of the biotin molecules with avidin, streptavidin or antibiotin antibodies is then carried out, wherein the avidin, streptavidin or the antibodies are conjugated to such signalling components as latex particles (Sodja, A., et al. supra, or Manning, et al Chromosoma, supra,) ferritin (Broker, supra a fluorogen such as fluorescein, an enzyme, secondary antibodies, magnetic particles, or the like.

DETAILED DESCRIPTION OF PREFERRED EMBODIMENTS

TRANSAMINATION OF THE MODIFIED NUCLEIC ACID STRAND

Dried nucleic acids are dissolved in a transamination mix, each milliliter of the transamination mix containing 560 mg hexanediamine hydrochloride, 23 mg 4-morpholineethane sulfonic acid (MES), and 100 mg sodium metabisulfite adjusted to pH6. The mixture is then set aside at room temperature for twenty four to seventy two hours. After this time the pH is raised to 8.5 for two hours and then lowered to 7.0. The transaminated nucleic acid is then isolated by gel filtration on Sephadex G-50.

Preparation of Aldehyde Paper

The aldehyde paper used may be prepared by limited oxidation of cellulose paper by periodate or can be purchased from commercial sources such as Sterogene Biochemicals, San Gabriel, Calif. The paper is cut into appropriate size.

Immobilization of Nucleic Acids On to Aldehyde Paper

The transaminated nucleic acid is dissolved in phosphate buffer pH 7.5 and sodium cyanoborohydride is added to make the concentration of sodium cyanoborohydride 0.1 molar. This solution is then applied to the paper at desired locations and concentration manually or mechanically. After application of the transamination mix, the paper is incubated in a humidity chamber for approximately two hours. After this time the whole paper is soaked in a solution of 1.0 molar aminocaproic acid and 0.1 molar cyanoborohydride for thirty minutes. The paper is then washed with 0.5 molar sodium chloride for fifteen minutes followed by two washings with phosphate buffered saline (PBS) for thirty minutes each. The paper is dried between two sheets of filter paper and stored in the dark over a desiccant such as Drierite.

Characterization of Paper

The presence of immobilized nucleic acids on the paper is shown by exposing this paper to labeled DNA complementary to the nucleic acids immobilized on the paper. After washing the label is detected on the region where the nucleic acid was immobilized.

EXAMPLE

Transamination An Oligonucleotide 5.6 grams of hexanediamine dihydrochloride were put into a 50 ml screw cap tube and dissolved in 0.231 grams of 4-morpholineethane sulfonic acid (MES) in 500 ul 10 M NaOH. The volume is then brought up to 9.5 mls with warm $H_2O$. The tube is then shaken until all the solid is dissolved.

1.0 grams of $NaS_2O_5$ is added to the screw cap tube and shaken. The pH is adjusted to 6.0 with concentrated HCl. The solution is allowed to stand for thirty minutes, and the pH is checked and readjusted to 6.0 by adding more HCl if necessary.

2 ml of the solution is added to 100–200 nmoles of dried oligonucleotide in a test tube. The tube is then covered with parafilm and shaken at room temperature for three days. After three days, the pH of the solution is brought up to 8.3 with NaOH and incubated for two hours. The pH is then reduced to 7.0 with HCl and incubated for thirty minutes.

The transaminated oligo is purified over the a Sephadex G-50 column using 10 mM triethyl ammonium bicarbonate (TEAB) as the buffer.

Attachment of Oligonucleotides To Aldehyde Cellulose Paper Using A Mechanical Sprayer The transaminated modified nucleic acid strands were immobilized onto aldehyde paper by spraying them onto the aldehyde paper with a sprayer (CAMAG Linomat IV Machine, CAMAG Scientific, Inc., Wrightsville Beach, N.C.) according to the manufacturer's instructions.

Aldehyde paper (BioBind C, Sterogene Biochemicals, San Gabriel, Calif.) was cut to an appropriate size (185 mm $\times \sim 15$ mm is a suitable size) and aligned on the sprayer.

The following reagents were combined:
a. Transaminated oligonucleotide at appropriate amount (For a paper 185 mm long, an oligonucleotide concentration of 100 pmoles/$c^2$, and assuming that the line the oligonucleotide will be on is 2 mm wide, use 370 pmoles of oligonucleotide.)
b. 5 ul 2M $KHPO_4$ pH 7.5
c. $H_2O$ to 90 ul 10 ul 1.0 M $NaCNBH_4$ was then added to the oligonucleotide mixture for a final volume of 100 ul. The mixture was then placed into a syringe and inserted into the spraying machine.

The transaminated modified nucleic acid strand was sprayed onto the aldehyde paper in 2 mm wide stripes. When spraying was done, the aldehyde paper was removed from the sprayer and incubated in a humidity chamber for two hours at room temperature.

The aldehyde paper was then placed in 1 M amino caproic acid +0.1 M sodium cyanoborohydride for thirty minutes at room temperature and afterwards washed for fifteen minutes at room temperature in 0.5 M NaCl. The paper was subsequently washed twice for thirty minutes each time at room temperature in 1 volume of PBS. The paper was dried between two pieces of filter paper and stored in the dark on the presence of a desiccant (Drierite).

Characterization Of Oligo dT Paper

The paper is cut into strips about 5 mM wide and one of the strips is put in a test tube containing a poly A sequence containing approximately 10% biotinylated uridine residues. This biotin containing poly A rises up by capillary action. After all the solution is drawn up, the strip is transferred to another tube containing 200 $\mu$l of streptavidin gold. After a few minutes, one sees a dark reddish brown band at the location where oligo dT was immobilized.

We claim:

1. A method of immobilizing nucleic acid to a solid surface having free aldehyde groups comprising the steps of:
   (a) providing a modified nucleic acid strand comprising a variable portion and an anchor portion wherein said variable portion comprises a nucleotide sequence having a selected base sequence and said anchor portion comprises from two to about 10 nucleotide bases modified with a primary amine function or nucleotide base equivalents having a primary amine function; and
   (b) reacting the primary amine functions of said anchor portion of said modified nucleic acid strand with the free aldehyde groups of said solid surface in a preselected pattern in the presence of a reducing agent to form complexes of said modified nucleic acid strand and at least a portion of said free aldehyde groups, such that said modified nucleic acid strand is attached to said solid surface through the primary strand functions of said anchor portion.

2. The method of claim 1 wherein said reducing agent is sodium cyanoborohydride.

3. The method of claim 1 wherein said solid surface is cellulose paper having free aldehyde groups on its surfaces.

4. The method of claim 1 wherein said anchor portion comprises from about five to about eight nucleotide bases or nucleotide base equivalents.

5. The method of claim 1 wherein said nucleotide base or nucleotide base equivalent is cytosine having nitrogen at the exocyclic 4 position of the pyrimidine ring modified with a substituent having a primary amine function.

6. The method of claim 1 wherein said variable portion is from about two to about 1,000 nucleotide bases in length.

7. The method of claim 6 wherein said variable portion is from about 15 to about 100 nucleotide bases in length.

8. The method of claim 1 wherein said variable portion of the modified nucleotide strand is a homopolymer.

9. The method of claim 8 wherein said homopolymer is poly thymidine.

10. The method of claim 8 wherein said homopolymer is poly adenine.

11. The method of claim 1 wherein said variable portion is RNA.

12. The method of claim 1 wherein said variable portion is DNA.

13. The method of claim 1 wherein said variable portion is of human origin.

14. The method of claim 1 wherein said variable portion is of bacterial origin.

15. The method of claim 1 wherein said variable portion is of viral origin.

16. The method of claim 1 wherein said variable portion is of fungal origin.

17. The method of claim 1 further comprising the step of reacting unreacted aldehyde groups from step (b) with a mixture of an amino acid and a reducing agent.

18. The method of claim 17 wherein said amino acid is α-amino caproic acid.

19. A solid surface for conducting nucleic acid hybridization assays comprising
   a solid surface prepared in accordance with the method of claim 1.

20. A solid surface for conducting nucleic acid hybridization assays comprising
   a solid surface prepared in accordance with the method of claim 8.

21. A kit for performing a nucleic hybridization assay comprising,
   a solid surface of claim 19 and at least one labeled nucleic acid probe, said solid surface and said at least one nucleic acid probe selected to form a detection system for a target strand of nucleic acid.

22. A kit for performing a nucleic hybridization assay comprising,
   a solid surface of claim 20 and at least one labeled nucleic acid probe, said solid surface and said at least one nucleic acid probe selected to form a detection system for a target strand of nucleic acid.

* * * * *

UNITED STATES PATENT AND TRADEMARK OFFICE
CERTIFICATE OF CORRECTION

PATENT NO. : 5,215,882
DATED : June 1, 1993
INVENTOR(S) : Bahl et al.

It is certified that error appears in the above-identified patent and that said Letters Patent is hereby corrected as shown below:

Claim 1, column 9, line 24, "primary strand" should be -- primary amine -- .

Signed and Sealed this

Fifteenth Day of March, 1994

Attest:

BRUCE LEHMAN

*Attesting Officer*    *Commissioner of Patents and Trademarks*